(12) United States Patent
Weiman

(10) Patent No.: US 9,005,256 B2
(45) Date of Patent: *Apr. 14, 2015

(54) VERTICAL INLINE PLATE

(71) Applicant: Globus Medical, Inc., Audubon, PA (US)

(72) Inventor: Mark Weiman, Coatesville, PA (US)

(73) Assignee: Globus Medical, Inc.

( * ) Notice: Subject to any disclaimer, the term of this patent is extended or adjusted under 35 U.S.C. 154(b) by 0 days.

This patent is subject to a terminal disclaimer.

(21) Appl. No.: 14/286,680

(22) Filed: May 23, 2014

(65) Prior Publication Data

US 2014/0257406 A1 Sep. 11, 2014

Related U.S. Application Data

(63) Continuation of application No. 12/614,067, filed on Nov. 6, 2009, now Pat. No. 8,795,340.

(60) Provisional application No. 61/112,442, filed on Nov. 7, 2008.

(51) Int. Cl.
 *A61B 17/70* (2006.01)
 *A61B 17/80* (2006.01)
 *A61B 17/56* (2006.01)

(52) U.S. Cl.
 CPC ......... *A61B 17/7059* (2013.01); *A61B 17/8042* (2013.01); *A61B 17/809* (2013.01); *A61B 2017/564* (2013.01)

(58) Field of Classification Search
 USPC .............. 606/70, 71, 280, 282–289, 291
 See application file for complete search history.

(56) References Cited

U.S. PATENT DOCUMENTS

| | | | | |
|---|---|---|---|---|
| 4,297,993 A * | 11/1981 | Harle | ............ | 606/70 |
| 4,905,679 A * | 3/1990 | Morgan | ............ | 606/70 |
| 4,905,680 A * | 3/1990 | Tunc | ............ | 606/280 |
| 5,108,399 A * | 4/1992 | Eitenmuller et al. | ............ | 606/77 |
| 5,549,612 A * | 8/1996 | Yapp et al. | ............ | 606/293 |
| 5,733,287 A * | 3/1998 | Tepic et al. | ............ | 606/280 |
| 5,772,662 A * | 6/1998 | Chapman et al. | ............ | 606/281 |
| 6,989,012 B2 * | 1/2006 | LeHuec et al. | ............ | 606/914 |
| 7,052,499 B2 * | 5/2006 | Steger et al. | ............ | 606/291 |
| 7,438,715 B2 * | 10/2008 | Doubler et al. | ............ | 606/71 |
| 2003/0181912 A1 * | 9/2003 | Michelson | ............ | 606/61 |
| 2004/0097937 A1 * | 5/2004 | Pike et al. | ............ | 606/69 |
| 2004/0210221 A1 * | 10/2004 | Kozak et al. | ............ | 606/69 |
| 2004/0215195 A1 * | 10/2004 | Shipp et al. | ............ | 606/69 |
| 2005/0010226 A1 * | 1/2005 | Grady et al. | ............ | 606/69 |
| 2005/0033294 A1 * | 2/2005 | Garden et al. | ............ | 606/61 |
| 2005/0065522 A1 * | 3/2005 | Orbay | ............ | 606/69 |
| 2005/0071006 A1 * | 3/2005 | Kirschman | ............ | 623/17.11 |
| 2005/0149027 A1 * | 7/2005 | Campbell et al. | ............ | 606/70 |
| 2005/0177161 A1 * | 8/2005 | Baynham et al. | ............ | 606/69 |
| 2005/0177162 A1 * | 8/2005 | McLeod et al. | ............ | 606/70 |
| 2006/0004361 A1 * | 1/2006 | Hayeck et al. | ............ | 606/69 |
| 2006/0229618 A1 * | 10/2006 | Dube | ............ | 606/69 |
| 2008/0015701 A1 * | 1/2008 | Garcia et al. | ............ | 623/17.16 |
| 2010/0004691 A1 * | 1/2010 | Amato et al. | ............ | 606/280 |

* cited by examiner

*Primary Examiner* — Pedro Philogene
*Assistant Examiner* — Lynnsy Summitt

(57) ABSTRACT

A spinal plate having an upper surface and a lower surface, the lower surface adapted to contact bone. A plurality of holes extend from the upper surface to the lower surface through the plate which is configured and adapted to receive bone fasteners for fixing the spinal plate to bone. At least one set screw receiving hole adjacent from each one of the plurality of holes, the set screw receiving hole configured to adapt with a set screw. The lower surface of the spinal plate comprises a ridge that protrudes from the underside of the plate and encloses the plurality of holes spaced inward from the perimeter of the spinal plate.

17 Claims, 5 Drawing Sheets

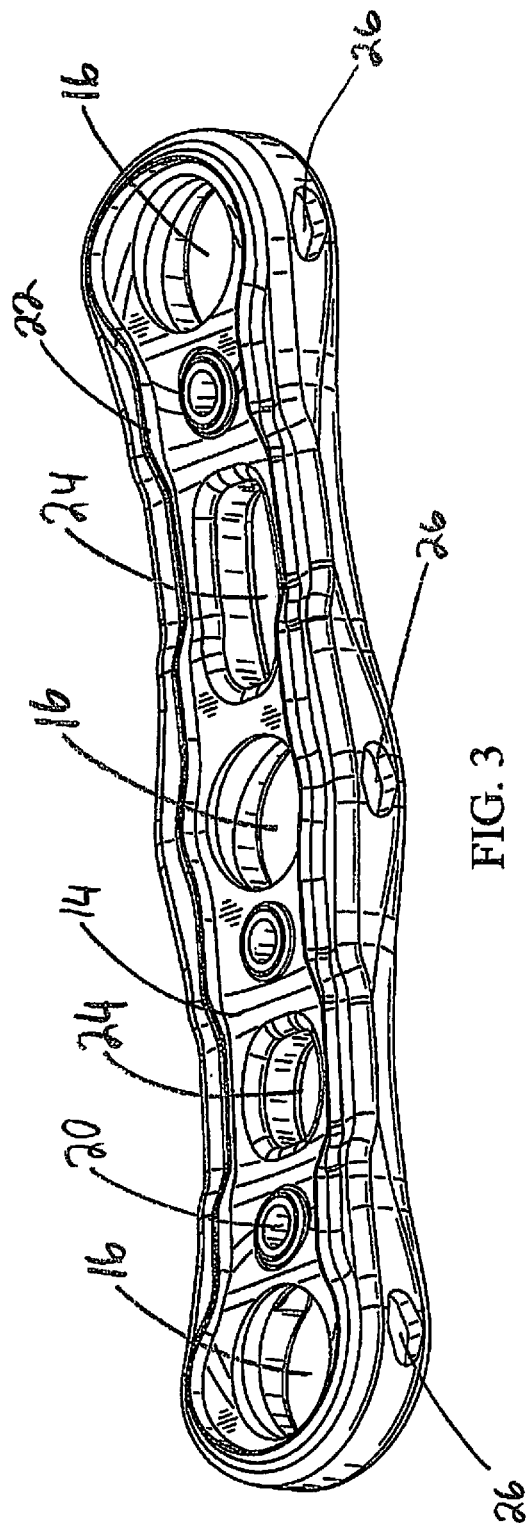
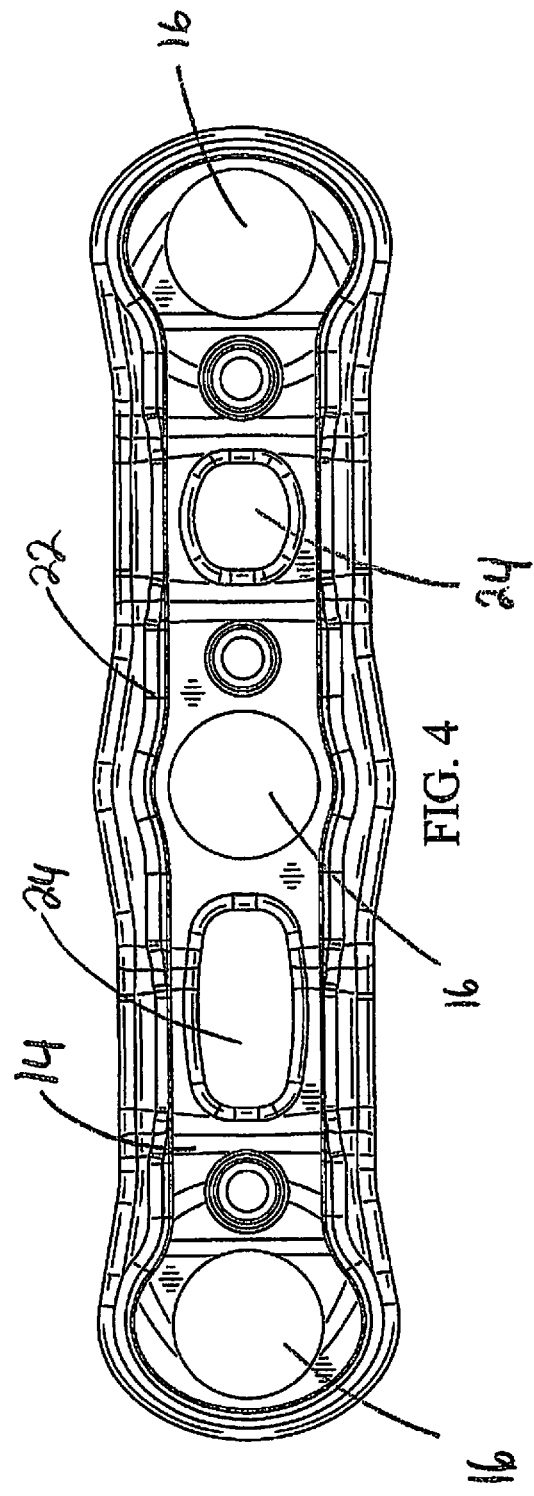
FIG. 3
FIG. 4

10

10

26
26
26

VERTICAL INLINE PLATE

CROSS-REFERENCE TO RELATED APPLICATIONS

This application is a continuation application of U.S. patent application Ser. No. 12/614,067 filed on Nov. 6, 2009 which claims priority to the U.S. Provisional Application Ser. No. 61/112,442 filed on Nov. 7, 2008, which is incorporated herein by reference in its entirety.

FIELD OF THE INVENTION

The present disclosure generally relates to a fixation device for positioning and immobilizing at least two adjacent vertebra. In particular, the present invention relates to an anterior cervical plate that immobilizes at least two adjacent vertebra.

BACKGROUND

Bones and bony structures are susceptible to a variety of weaknesses that can affect their ability to provide support and structure. Weaknesses in bony structures may have many causes, including degenerative diseases, tumors, fractures, and dislocations. Advances in medicine and engineering have provided doctors with a plurality of devices and techniques for alleviating or curing these weaknesses.

Typically, weaknesses in the spine are corrected by using devises that fuse one or more vertebrae together. Common devices involve plate systems that align and maintain adjacent cervical vertebrae in a desired position, with a desired spacing.

These devises, commonly referred to as bone fixation plating systems, typically include one or more plates and screws for aligning and holding vertebrae in a fixed position with respect to one another. Initial devices used stainless steel plates and screws. In order to remain fixed in place, the screws were required to pass completely through the vertebrae and into the spinal canal. These systems generally rely on four or more screws. This also causes problems when part of one of the vertebra being screwed into is diseased or fractured.

Thus, there is a need for a plate system that is small in width and provides similar structural stability as the larger plate system.

SUMMARY OF THE INVENTION

A spinal plate having an upper surface and a lower surface, the lower surface adapted to contact bone. A plurality of holes extend from the upper surface to the lower surface through the plate which is configured and adapted to receive bone fasteners for fixing the spinal plate to bone. At least one set screw receiving hole adjacent from each one of the plurality of holes, the set screw receiving hole configured to adapt with a set screw. The lower surface of the spinal plate comprises a ridge that protrudes from the underside of the plate and encloses the plurality of holes spaced inward from the perimeter of the spinal plate.

BRIEF DESCRIPTION OF THE ILLUSTRATED EMBODIMENTS

FIG. 3 is a bottom perspective view of the vertical inline plate according to the present invention;

FIG. 4 is a bottom view of the vertical inline plate according to the present invention;

DETAILED DESCRIPTION OF THE ILLUSTRATED EMBODIMENTS

Figure 1:
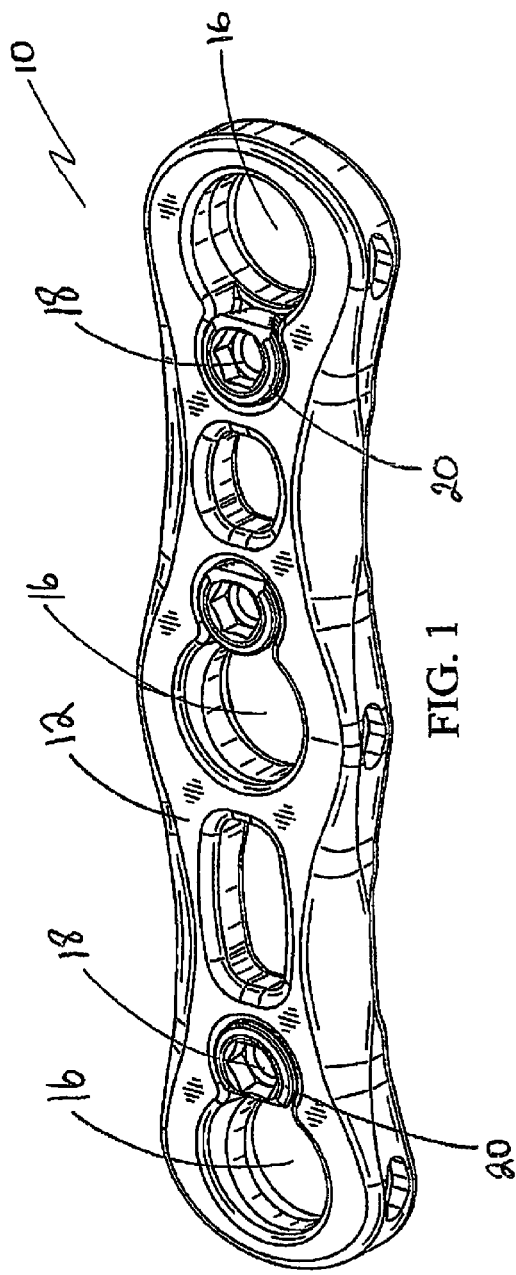
FIG. 1 is a top perspective of the vertical inline plate according to the present invention.
Figure 2:
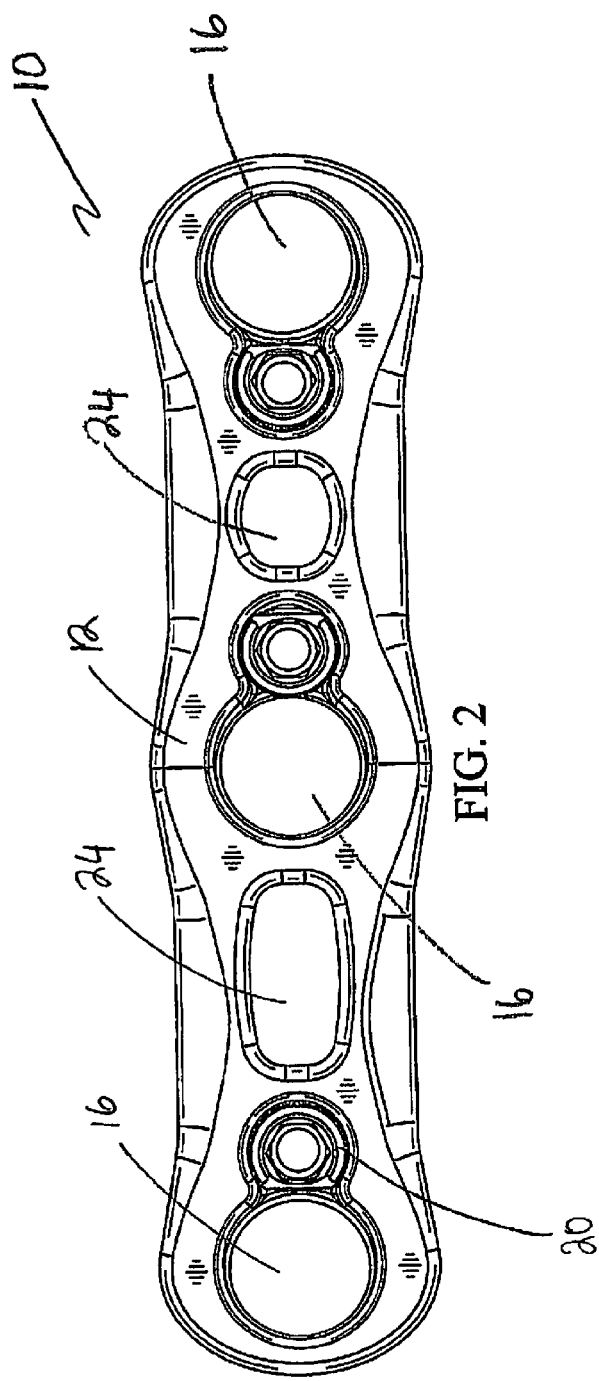
FIG. 2 is a top view of the vertical inline plate according to the present invention.
Figure 5:
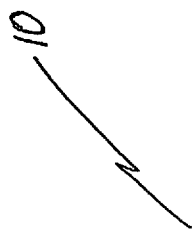
FIG. 5 and FIG. 6 are front and back views of the vertical inline plate according to the present invention.
Figure 6:
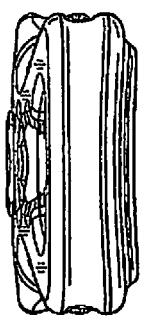
Figure 6:
Figure 7:
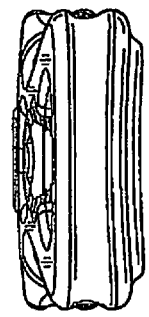
FIG. 7 and FIG. 8 are side views of the vertical inline plate according to the present invention.
Figure 7:
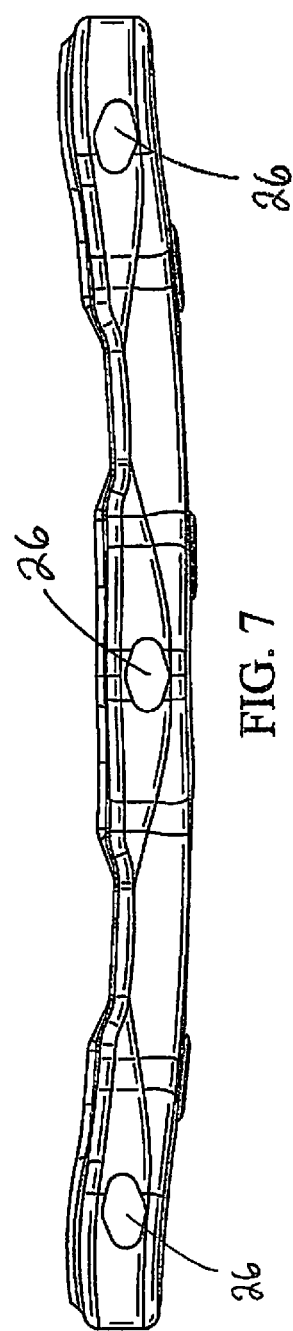
Figure 8:
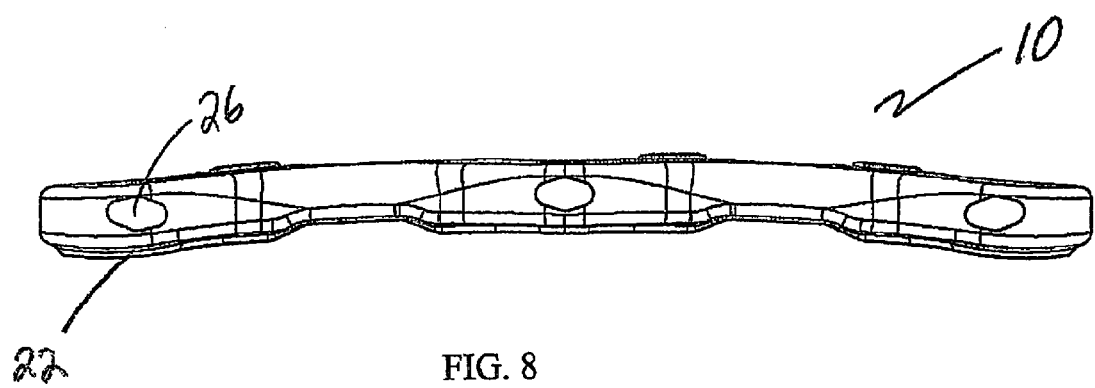

FIGS. 1-4 illustrate a top view and a bottom view of a bone plate 10 according to the preferred embodiment of the present invention. The bone plate 10 comprises an upper surface 12 and a lower surface 14, with the lower surface 14 configured to contact bone. The bone plate 12 may further have a plurality of holes 16 configured and adapted to receive fasteners, such as, for example, screws that will affix the bone plate to the bone. The bone plate 10 is contoured in two directions in order to match the lordotic and medial lateral curvatures of the spine.

The bone plate 10 is further configured with a spherical hole 18 adjacent to each one of the plurality of holes 16 that is adapted to receive a set screw 20. The set screw 20 blocks each one of the bone screws from coming out of the bone plate 10 so that the bone screw will not back out of the plate even if the screw shaft loses purchase with the surrounding bone, which can occur in patients having substandard bone structure resulting from osteoporosis or other factors.

On the bottom portion of the bone plate 10, a single continuous ridge 22, as shown in FIGS. 3 and 4, extend around the edge of the plate 10 surrounding the plurality of holes 16. Specifically, the ridge 22 protrudes from the bottom surface 14 of the bone plate 10 and may be embedded within a vertebrae when the bone plate is installed. The contact between the ridge 22 and the bone provides bone purchase in addition to that provided by the bone screws. The ridge 22 also allows for torsional stability between the plate 10 and the bone. The ridge 22 may be configured to be in any shape that can grip a structure composed of bone. The ridge 22 and the bone plate 10 are a single piece of titanium alloy, but may be made of any material possessing superior strength which is compatible with the human body.

The bone plate 10 is also provided with graft windows 24 that extend from the upper surface 12 to the lower surface 14, that may be symmetrically or asymmetrically. Graft materials and synthetic proteins may be placed within these windows 24 to accelerate bone grown between the two adjacent vertebrae. The bone plate 10 is also provided with a reduced cross sectional area in between the bone screw holes 16 in order to more easily fit the anatomy as well as to allow for and isolate the bending of the plate in these zones.

The size of the bone plate 10 may be of any appropriate size required to perform its function. The length of the bone plate 10 maybe within a range of about 8 millimeters to 34 millimeters for plates used to stabilize one level of the cervical spine. A bone plate 10 used to stabilize two levels in the cervical spine have the length within the range of about 18 millimeters to about 54 millimeters. The optimal length for a one level bone plate is between 13 millimeters and 26 millimeters. The optimal length of a two level bone plate is between 26 millimeters to 46 millimeters. The width of the bone plate is between 8 millimeters and 20 millimeters. However, the optimal width of the bone plate is between 1.0 and 14 millimeters according the preferred embodiment. The size and geometry of the plate system according to the present invention enables surgeon with easier access to the anterior elements of the spine. The reduced number of screw holes to fasten the plate with the vertebrae allows reduces the risks associated with fastening additional screws into spine as accomplished by the larger spinal plate system.

FIGS. 5, 6, 7, and 8 illustrate the front, back and a side view of the bone plate 10. The bone plate 10 also has tool engagement features on the sides of the plate. Specifically, on the sides of the bone plates, there are provided a plurality of depressions positioned for engaging with an instrument. The engaging instrument contacts the bone plate and enables the surgeon or user to control the plate so that, it is placed in the proper position in the boney elements of the spine. The shape of these depressions allow for the ability to have the screws positioned through a fixed or variable angle connection.

Figure 9:
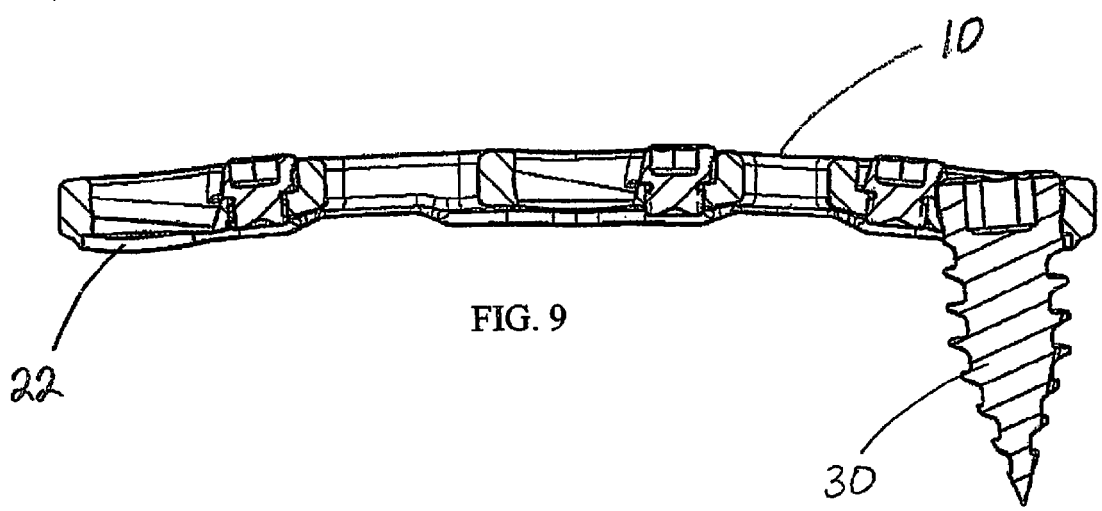
FIG. 9 illustrates as side view of the vertical inline plate and a bone fastener according to the present invention.
Figure 10:
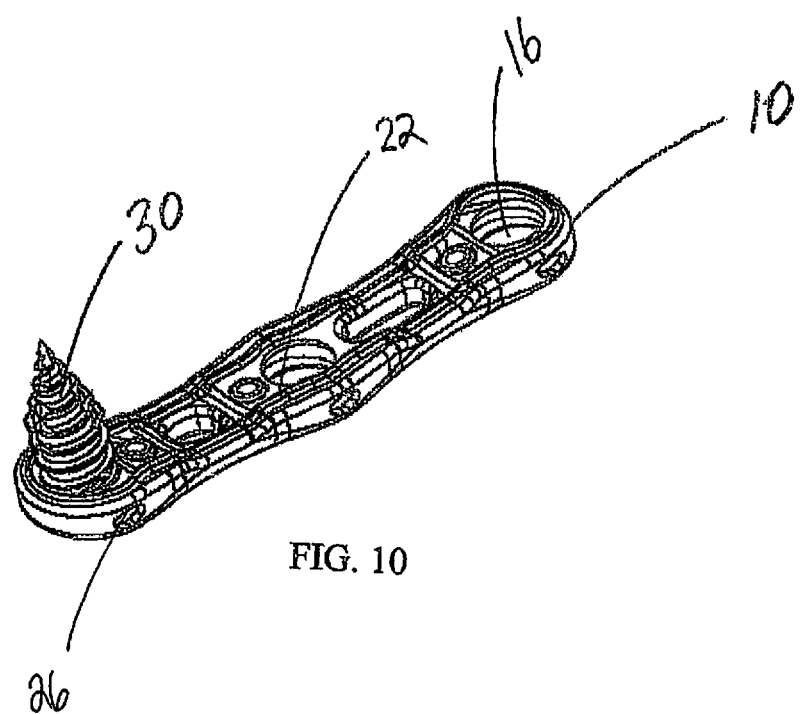
FIG. 10 illustrates a bottom perspective view of the vertical inline plate and bone fastener according to the present invention.

FIGS. 9 and 10 illustrate the bone plate 10 and a bone fastener or screw. The screw 30 used to connect the bone plate to the bone are provided with a spherical head that is selectively engageable with the spherical curvature of the hole. An elongate shaft is connected to the spherical head to allow it to penetrate the bony tissue of the vertebrae. Preferably, the elongate shaft includes threads that aid in fixing the plate to a vertebra. It is also desirable to have a hexagonal projection to aid in gripping the screw. The length of the elongate shaft may be varied as desired. In one embodiment, the length of the elongate shaft is about 20 millimeters or less. In another embodiment, the length of the elongate shaft is about 10 millimeters or less. In yet another embodiment, the length of the elongate shaft is about 5 millimeters or less.

The cervical plate system is attached to at least two vertebrae in the cervical region of the spine. This region is generally accessed anterioraly. A partial or complete discectomy is performed for the possible placement of a spacer between the two adjacent vertebrae which enhances fusion between the vertebrae. The plate is positioned over the two adjacent vertebrae with the graft windows being positioned so that the disc space is accessible through the window. Bone screws are screwed into the vertebrae through the screw hole in the plate. The center of the screw holes are positioned on a central axis of the plate. The plate system according to the present invention provides the stability to allow fusion to occur between the adjacent vertebra with minimal discomfort to the patient and reduces the negative effects caused by larger plate system.

While it is apparent that the invention disclosed herein is well calculated to fulfill the objects stated above, it will be appreciated that numerous modifications and embodiments may be devised by those skilled in the art.

I claim:

1. A method for stabilizing vertebrae comprising:
    providing a spinal plate comprising:
        an upper surface and a lower surface, the lower surface adapted to contact bone;
        a plurality of holes extending from the upper surface to the lower surface through the plate configured and adapted to receive bone fasteners for fixing the spinal plate to bone;
        at least one set screw receiving hole adjacent from each one of the plurality of holes, the set screw receiving hole configured to adapt with a set screw;
        wherein the lower surface of the spinal plate comprises a single continuous ridge protruding from the lower surface and spaced inward from a perimeter of the spinal plate, the single continuous ridge extending around the entire perimeter of the spinal plate
        wherein the single continuous ridge is positioned between the perimeter of the spinal plate and the plurality of holes,
    positioning the spinal plate on adjacent vertebra.

2. The method of claim 1, further comprising at least one graft window extending from the upper surface to the lower surface of the spinal plate.

3. The method of claim 1, wherein the spinal plate comprises a plurality of depressions positioned on a side portion of the spinal plate for engaging with an instrument so that the bone fastener can be inserted in a fixed or variable angle.

4. The method of claim 1, wherein the spinal plate has a length within the range of 8 millimeters to 54 millimeters.

5. The method of claim 1, wherein the spinal plate has a width within the range of 10 millimeters to 14 millimeters.

6. The method of claim 1, wherein a height of the spinal plate is decreased at a position between the plurality of holes to facilitate in bending of the spinal plate.

7. The method of claim 1, wherein each one of the plurality of screw holes are positioned at an angle.

8. The method of claim 7, wherein each one of the set screw receiving holes adjacent to each one of the plurality of screw holes is configured at an angle different than that of the angle of the screw holes.

9. A method for stabilizing adjacent vertebrae comprising:
    providing a spinal plate comprising:
        an upper surface and a lower surface, the lower surface adapted to contact bone;
        a plurality of holes extending from the upper surface to the lower surface through the plate;
        at least one set screw receiving hole adjacent from each one of the plurality of holes, the at least one set screw receiving hole configured to adapt with a set screw;
        wherein the lower surface of the spinal plate comprises a single continuous ridge protruding from the lower surface and spaced inward from a perimeter of the spinal plate, and at least one bone fastener adapted to be received within at least one of the plurality of holes,
        wherein the single continuous ridge extends around the entire perimeter of the spinal plate
        wherein the single continuous ridge is positioned between the perimeter of the spinal plate and the plurality of holes.

10. The method of claim 9, further comprising at least one graft window extending from the upper surface to the lower surface of the spinal plate.

11. The method of claim 9, wherein the spinal plate comprises a plurality of depressions positioned on a side portion of the spinal plate for engaging with an instrument so that the bone fastener can be inserted in a fixed or variable angle.

12. The method of claim 9, wherein the spinal plate has a length within the range of 8 millimeters to 54 millimeters.

13. The method of claim 9, wherein the spinal plate has a width within the range of 10 millimeters to 14 millimeters.

14. The method of claim 9, wherein a height of the spinal plate is decreased at a position between the plurality of holes to facilitate in bending of the spinal plate.

15. The method of claim 9, wherein each one of the plurality of screw holes is configured at an angle.

16. The method of claim 15, wherein each one of the set screw receiving holes adjacent to each one of the plurality of screw holes is configured at an angle different than that of the angle of the screw holes.

17. A method for stabilizing vertebrae comprising:
providing a spinal plate comprising:
- an upper surface and a lower surface, the lower surface adapted to contact bone;
- a plurality of holes extending from the upper surface to the lower surface through the plate configured and adapted to receive bone fasteners for fixing the spinal plate to bone;
- at least one set screw receiving hole adjacent from each one of the plurality of holes, the set screw receiving hole configured to adapt with set screw;
- wherein the lower surface of the spinal plate comprises a single continuous ridge protruding from the lower surface and spaced inward from a perimeter of the spinal plate and extending along the entire perimeter of the spinal plate, the single continuous ridge being positioned between the entire perimeter of the spinal plate and the plurality of holes,
- wherein the spinal plate is configured with a lordotic configuration, positioning the spinal plate on vertebrae.

* * * * *